United States Patent
Nakano

(10) Patent No.: US 7,759,083 B2
(45) Date of Patent: Jul. 20, 2010

(54) SCREENING METHOD FOR A GROWTH INHIBITOR OR PROMOTER OF A VASCULAR SMOOTH MUSCLE CELL

(75) Inventor: Toru Nakano, Toyonaka (JP)

(73) Assignee: Shionogi & Co., Ltd., Osaka-Shi, Osaka (JP)

(*) Notice: Subject to any disclaimer, the term of this patent is extended or adjusted under 35 U.S.C. 154(b) by 725 days.

(21) Appl. No.: 11/596,894

(22) PCT Filed: May 24, 2005

(86) PCT No.: PCT/JP2005/009397

§ 371 (c)(1),
(2), (4) Date: Nov. 17, 2006

(87) PCT Pub. No.: WO2005/116649

PCT Pub. Date: Dec. 8, 2005

(65) Prior Publication Data

US 2008/0268484 A1 Oct. 30, 2008

(30) Foreign Application Priority Data

May 26, 2004 (JP) .................. 2004-155749

(51) Int. Cl.
*C12Q 1/56* (2006.01)

(52) U.S. Cl. .................. 435/13; 435/252.3; 435/320.1

(58) Field of Classification Search .................. 435/13, 435/252.3, 320.1
See application file for complete search history.

(56) References Cited

U.S. PATENT DOCUMENTS

| 6,525,023 B1 | 2/2003 | Yamasaki et al. |
| 2003/0134796 A1 | 7/2003 | Roemisch et al. |

FOREIGN PATENT DOCUMENTS

| JP | 2002-112798 A | 4/2002 |
| JP | 2003-183178 A | 7/2003 |
| WO | WO 99/55863 A1 | 11/1999 |
| WO | WO 99/55864 A1 | 11/1999 |

OTHER PUBLICATIONS

Hedin U et al: "Antithrombin III inhibits thrombin-induced proliferation in human arterial smooth muscle cells." Arteriosclerosis and Thrombosis: A Journal of Vascular Biology/ American Herat Association Feb. 1194, vol. 14, No. 2, Feb. 1994, pp. 254-260, XP002476100.

(Continued)

*Primary Examiner*—Tekchand Saidha
(74) *Attorney, Agent, or Firm*—Birch, Stewart, Kolasch & Birch, LLP

(57) ABSTRACT

It was found that TAT which has not been known biological activity has a role as a new blood vessel smooth muscle proliferation factor, and then a screening method vascular of an inhibitor or promoter of a smooth muscle cell growth with TAT is established.

7 Claims, 1 Drawing Sheet

OTHER PUBLICATIONS

Bar-Shavit R et al: "Binding of thrombin to subendothelial extracellular matrix. Protection and expression of functional properties." The Journal of Clinical Investigation Oct. 1989, vol. 84, No. 4 Oct. 1989 XP002476101.

Database WPI Week 200248, Derwent Publications Ltd., London GB; AN 2002-448760, XP002476102.

Ota et al., Japanese Journal of Clinical Medicine, vol. 57, 1999 Nen Zokango, pp. 585-587.

Ross, N. Engl. J. Med., vol. 314, pp. 488-500, Feb. 20, 1986.

Morishita et al., Proc. Natl. Acad. Sci. U.S.A., vol. 90, pp. 8474-8478, Sep. 1993.

Ferns et al., Science, vol. 253, p. 1129, Sep. 6, 1991.

Gospodarowicz et al., Endocrinology, vol. 118, pp. 82-90 (1986).

Williams et al., Proc. Natl. Acad. Sci. U.S.A., vol. 79, pp. 5867-5870, Jul. 7, 1982.

Majack et al., Proc. Natl. Acad. Sci. U.S.A., vol. 83, pp. 9050-9054, Aug. 21, 1986.

Dabbagh et al., Thromb Haemost, vol. 79, pp. 405-409 (1998).

Hao et al., Arterioscler Thromb Vasc Biol., vol. 23, pp. 1510-1520, May 14, 2003.

Song et al., Biochemica et Biophysica Acta 1573, Apr. 12, 2002, pp. 241-246.

[Figure 1]
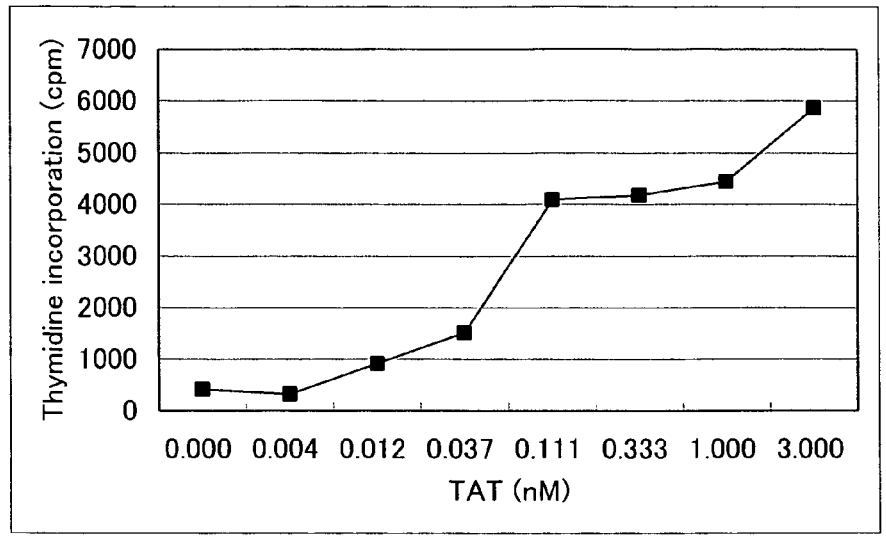
[Figure 2]
sense
5'-GATCCC----------------TTCAAGAGA----------------TTTTTTGGAAA-3'
antisense
5'-GGCCTTTCCAAAAAA----------------TCTCTTGAA----------------GG-3'
[Figure 3]
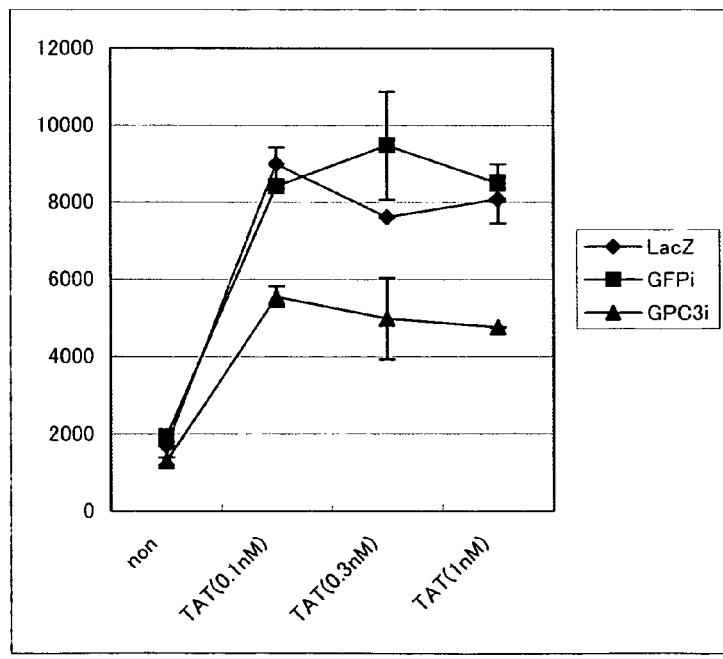

SCREENING METHOD FOR A GROWTH INHIBITOR OR PROMOTER OF A VASCULAR SMOOTH MUSCLE CELL

This application is the National Stage of International Application PCT/JP2005/009397, filed May 24, 2005, which claims priority under 35 USC §119(a)-(d) of Japanese Application No. 2004-155749, filed May 26, 2004.

FIELD OF THE INVENTION

This invention relates to a screening method for a growth inhibitor or promoter of a vascular smooth muscle cell.

PRIOR ART

Proliferation of vascular smooth muscle cells is considered to be caused by vascular endothelial cell injury by oxidized low density lipoprotein, vascular internal injury by wall shear stress stimulus associated with hypertension or blood flow or the like, external injury by wound, Percutaneous Transluminal Angioplasty by balloon or the like, or organ transplantation. That is to say, it is thought that vascular smooth muscle cells proliferate in a living body to recover from injury by wound or the like. On the basis of these findings, it is known that proliferation of vascular smooth muscle cells effects healing of wound or the like.

On the other hand, overproliferation of vascular smooth muscle cells causes vascular wall thickening, stenosis or occlusion of vascular lumen and triggers the arteriosclerotic diseases such as atherosclerosis, diabetic vascular injury, cerebral ischemia attack, angina and myocardial infarction (Non-patent Document 1). On the basis of these findings, it is thought that inhibition of proliferation of vascular smooth muscle cells leads to prevention and treatment of the above arteriosclerotic disease (Non-patent Document 2). The development of an inhibitor of vascular smooth muscle cell growth for arteriosclerotic diseases has been tried (Non-patent Document 3).

As a screening method for a growth inhibitor of vascular smooth muscle cells, a method with a polypeptide which is searched with a method that cDNA having a sequence coding a signal peptide can be easily selected (SST method) and which inhibits proliferation of vascular smooth muscle cells (Patent Document 1 and 2), a method by using blood vessel smooth muscle proliferation promoting activity (Patent Document 3) or the like has been reported.

Fibroblast growth factor (FGF) (Non-patent Document 4), Platelet-derived growth factor (PDGF) (Non-patent Document 5), thrombospondin (Non-patent Document 6) and vascular smooth muscle cell growth factor (VSGF) (Patent Document 4) have been known as factors with vascular smooth muscle cell proliferation promoting activity. Additionally, it is known that thrombin activates PAR-1 by protease activity and the activated PAR-1 relates to vascular smooth muscle cell proliferation (Non-patent Document 7). It is disclosed that the rate of crisis of vascular injury in transplant and the degree of blood vessel wall proliferation decreased by antithrombin III in an animal experiment with rats that homologous hearts are heterotopic transplanted, therefore, antithrombin III is an agent or active ingredient which is appropriate for prevention and/or treatment of vascular proliferation diseases (Patent Document 5).

Vascular smooth muscle cells composing vascular media had been considered as a group of homogeneous cells, however, the recent research disclosed that the vascular media is a group of various smooth muscle cells having various characters concerning proliferation potency, form or the like (Non-patent Document 3). Additionally, it is reported that smooth muscle cells in vascular intima thickened part has higher proliferation potency than smooth muscle cells prepared from the media. It is thought that a few cells having especially high proliferation potency in a group of various smooth muscle cells in the media relate to vascular wall thickening (Non-patent Document 8). However, a growth factor which relates to proliferation of these high proliferative vascular smooth muscle cells has not been identified.

Thrombin formed in blood vessel binds to antithrombin III-heparin complex, and then heparin is removed from this complex to form thrombin-antithrombin III complex (TAT). Because antithrombin III irreversibly binds to thrombin, protease activity of thrombin is inhibited. Because thrombin generated in blood rapidly disappears, the concentration can not be measured. However, the concentration of TAT can be measured and the increase is used as an indicator for accelerating of thrombin formation in blood vessel, that is to say, the tendency of thrombus (Non-patent Document 9). However, so far, there is no paper that biological activity of TAT is described and the relation of TAT and arteriosclerosis has not been reported.

Patent Document 1: WO99/55863

Patent Document 2: WO99/55864

Patent Document 3: JP2002-112798

Patent Document 4: JP1999-123092

Patent Document 5: JP2003-183178

Non-patent Document 1: Ross, R. et al., The New England Journal of Medicine (N. Engl. J. Med.), Vol. 314, 488-500 (1986)

Non-patent Document 2: Morishita, R. et al., Proceedings of the National Academy of Science (Proc. Natl. Acad. Sci. U.S.A.), Vol. 90, pp. 8474-8478 (1993)

Non-patent Document 3: Gordon, A, et al., Science, Vol. 253, pp. 1129 (1991)

Non-patent Document 4: Gospodarowicz, D. et al., Endocrinology, Vol. 118, pp. 82-90 (1986)

Non-patent Document 5: Antoniades, H. N. et al., Proceedings of the National Academy of Science (Proc. Natl. Acad. Sci. U.S.A.), Vol. 79, pp. 5867-5870 (1982)

Non-patent Document 6: Bornstein, P. et al., Proceedings of the national academy of science (Proc. Natl. Acad. Sci. U.S.A.), Vol. 83, pp. 9050-9054 (1986)

Non-patent Document 7: Dabbagh, K. et al., Thrombosis and Haemostasis (Thromb Haemost), Vol. 79, pp. 405-409 (1998)

Non-patent Document 8: Hao, H. et al., Arteriosclerosis, Thrombosis, and Vascular Biology (Arterioscler Thromb Vasc Biol.), Vol. 23, pp. 1510-1520 (2003)

Non-patent Document 9: Ota et al., Nippon Rinsyou, Vol. 57, pp. 585-587 (1999)

DISCLOSURE OF INVENTION

Problems to be solved by the Invention

This invention provides a screening method for a compound which inhibits proliferation of a vascular smooth muscle cell which is a cause of thickening of vascular wall in an arteriosclerotic disease. At the same time, it provides a screening method for a compound which promotes proliferation of a vascular smooth muscle cell as a candidate compound of a wound healing agent. In more detail, it provides a screening method for a compound which inhibits or promotes proliferation of a vascular smooth muscle cell by stimulation of thrombin-antithrombin III complex (TAT). One of purposes of this invention is that a vascular smooth muscle cell growth inhibitor or promoter is easily or rapidly screened by the screening method.

Means to Solve the Problems

This inventor has intensively studied to find a new growth factor of vascular smooth muscle cells. The new growth factor, TAT, has not been known biological activity at all. The inventor found that it has the function to proliferate some cells of vascular smooth muscle cells at very low concentration. Additionally, as a result of comparison between the expression genes in vascular smooth muscle cells which responds to TAT and the expression genes in vascular smooth muscle cells which does not respond to TAT, it is found that a gene coding a protein, Glypican 3, almost specifically expressed in cells which respond to TAT. Glypican 3 is a heparan sulfate proteoglycan which is known to highly expressed in fetus, lung, ovary or the like of adult, or hepatic cancer cells and it is suggested that it has the function to inhibit proliferation or cell survival in fetus (Biochemica et Biophysica Acta 1573 (2002) 241-246). However, contrary to our expectation, the reactivity of the cells against TAT and the cell proliferation potency decreased when expression of Glypican 3 was inhibited by RNAi technique in vascular smooth muscle cells which responds to TAT. On the basis of these findings, this inventor developed a screening method for a compound which inhibits or promotes proliferation of a vascular smooth muscle cell through a new mechanism.

This invention is, (1) A screening method for a compound or the salt which has activity to inhibit or promote proliferation of a vascular smooth muscle cell, comprising;

(A) a process to contact a vascular smooth muscle cell and a thrombin-antithrombin III complex under the absence of blood serum, and under the presence of or under the absence of a test compound, and then measure the degree of proliferation of the cell, and, (B) a process to compare the degree of proliferation of the cell under the presence of a test compound with that under the absence of a test compound, (2) The screening method of (1), wherein the vascular smooth muscle cell is a cell which responds to 0.1-0.5% blood serum and proliferates, (3) The screening method of (1), wherein the vascular smooth muscle cell is a cell which responds to a thrombin-antithrombin III complex and proliferates, (4) The screening method of (1), wherein the thrombin-antithrombin III complex is a human thrombin-antithrombin III complex, (5) The screening method of (1), wherein the vascular smooth muscle cell is a cell containing Glypican 3, (6) The screening method of (1), wherein the vascular smooth muscle cell is a transformant having Glypican 3 expression vector, (7) The screening method of any one of (1)-(6), wherein the process to measure the degree of proliferation of a vascular smooth muscle cell is a process to measure DNA synthesis level of the vascular smooth muscle cell, (8) The screening method of any one of (1)-(6), wherein the process to measure the degree of proliferation of a vascular smooth muscle cell is a process to measure cell population of the vascular smooth muscle cell, (9) The screening method of (5) or (6), wherein the process to measure the degree of proliferation of a vascular smooth muscle cell is a process to measure the expression level of Glypican 3 in the vascular smooth muscle cell,

(10) The screening method of any one of (1)-(6) for a therapeutic or preventive agent for an arteriosclerotic disease,

(11) A screening kit for a compound or the salt which has activity to inhibit or promote proliferation of a vascular smooth muscle cell for the screening method of any one of (1)-(6) and containing a thrombin-antithrombin III complex,

(12) A screening kit for a compound or the salt which has activity to inhibit or promote proliferation of a vascular smooth muscle cell for the screening method of any one of (1)-(6) and containing a vascular smooth muscle cell which responds to a thrombin-antithrombin III complex and proliferates,

(13) A growth promoter of a vascular smooth muscle cell comprising a thrombin-antithrombin III complex.

EFFECT OF THE INVENTION

A compound which has activity to inhibit or promote proliferation of a vascular smooth muscle cell can be easily and rapidly screened with a screening method of this invention. Additionally, with this screening method, a candidate compound of a therapeutic or preventive agent for an arteriosclerotic disease with inhibitory activity of proliferation of a vascular smooth cell through a mechanism relating to TAT which is different from a well-known mechanism can be screened. Furthermore, a candidate compound of a wound healing agent with promoting activity of proliferation of a vascular smooth cell through a mechanism relating to TAT which is different from a well-known mechanism can be screened.

BRIEF DESCRIPTION OF DRAWINGS

[FIG. 1] Proliferation of vascular smooth muscle cells by human TAT

[FIG. 2] DNA fragment constructive oligo DNA coding sh RNA

[FIG. 3] Proliferation of vascular smooth muscle cells whose GPC3 is knockdowned by human TAT

BEST MODE FOR CARRYING OUT THE INVENTION

"A screening method for a growth inhibitor or promoter of a vascular smooth muscle cell" of this invention is characterized by using TAT, which has not been known biological activity, and a vascular smooth muscle cell and screening for a candidate compound which inhibits or promotes proliferation of a vascular smooth muscle cell by stimulation of TAT.

Terms used in this description have the usual meanings in this field except for the case especially mentioned. Additionally, a well-known method is used as Gene Recombination Technology, a production engineering of a recombinant protein in a cell, a separation refining method of an expression protein, an assay, a molecular biological method, an immunochemical method or the like as long as there is no special direction in this description.

"A vascular smooth muscle cell" means a smooth muscle cell which mainly exists in vascular media. There are cells of various phenotypes as a vascular smooth muscle cell. A vascular smooth muscle cell for this invention can prepared by a well-known method, for example, with blood vessel of mammal, in particular, of human, monkey, cattle, rabbit, mouse, rat, hamster or the like, preferably artery of aorta or the like. A method to prepare a vascular smooth muscle cell is especially not restricted and can be selected an appropriate method according to a purpose of an experiment. It is, for example, an enzyme dispersion method that cell aggregation peeled from vascular wall is treated with an enzyme such as collagenase and cultured, explant culture method (explant method) that a small piece of blood vessel is fixed on a cultured dish, or the like. Additionally, commercially available a vascular smooth muscle cell can be used for this invention.

In this invention, any vascular smooth muscle cell can be used. Although there is a vascular smooth muscle cell which usually responds to 5-10% blood serum and proliferates, preferred is a vascular smooth muscle cell which especially responds to low concentration (about 0.1-0.5%) blood serum and proliferates. Furthermore, preferred is a vascular smooth muscle cell which responds to TAT and proliferates. Additionally, a vascular smooth muscle cell containing Glypican 3, that is, a vascular smooth muscle cell in which Glypican 3 express can be used. The vascular smooth muscle cell containing Glypican 3 can be a cell expressing Glypican 3 when it is prepared or a cell that Glypican 3 is artificially high expressed. As a method obtaining a vascular smooth muscle cell that Glypican 3 is artificially high expressed, a well-known method to highly express a protein in a cell can be used (Reference; Molecular Cloning Second Edition, Current Protocols in Molecular Biology supplement 1-38). A method to highly express a protein in a cell is, for example, a method to create a transormant with Glypican 3 expression vector.

Thrombin formed in blood vessel binds to an antithrombin III-heparin complex and then heparin removes from this complex to form a "thrombin-antithrombin III complex". Because antithrombin III irreversibly binds to thrombin, protease activity of thrombin is inhibited. Thrombin-antithrombin III complex (TAT) for this invention can be prepared by purifying thrombin and antithrombin III from, for example, blood serum of mammal, in particular, blood serum of human, monkey, cattle, rabbit, mouse, rat, hamster or the like by a well-known method and incubating them together. Thrombin and antithrombin III on the market can be used. Especially, human TAT is preferable.

The above incubation can be performed by mixing thrombin and antithrombin III in a solution which does not prevent the natural functions of protein and maintaining them under an appropriate reaction condition, for example, at an appropriate reaction temperature for an appropriate reaction time.

The above "a solution which does not prevent the natural functions of protein" is, for example, MOPS buffer, HEPES buffer, Tris buffer or the like.

The above "an appropriate reaction condition" is not especially restricted, for example, in a solution such as MOPS buffer, HEPES buffer or Tris buffer, at pH6.0-10.0, preferably at pH 7.0-8.0, and more preferably at pH 7.4, at 4° C.-50° C., preferably at 25° C.-40° C., and more preferably at 37° C., for 1-5 hour(s) and preferably for 3 hours, or the like. In more detail, the appropriate reaction condition is, for example, in 50 mM Tris (pH7.4) under the above condition.

"Blood serum" means transparent supernatant obtained by that blood cells and fibrin coagulate and separate when blood obtained from a living body put a rest. It contains various components which are necessary for maintenance of functions of a living body, for example, a protein such as albumin or globulin. To perform animal cell culture, it is essential that blood serum is added to a synthetic medium and blood serum of cattle, horse, human or the like can be used. A well-known method can be used as a preparation method of blood serum. For example, supernatant obtained from blood is extended and blood cells are excluded. The supernant is sterilized by filtration with a membrane filter. Bovine serum, especially fetal bovine serum (FBS), is generally used and can be used for culture of a vascular smooth muscle cell because it has good promoting activity of cell proliferation.

A screening method of this invention is characterized by performing under the absence of blood serum. Because blood serum itself causes proliferation of a vascular smooth muscle cell, the effect on proliferation of a vascular smooth muscle cell by TAT can not be exactly measured under the presence of it.

For example, in Examples, Dulbecco's Modified Eagle Medium medium (DMEM medium) containing 10% fetal calf serum (ICN) was used for culture of a vascular smooth muscle cell, however, it was changed to DMEM medium containing 0.05% bovine serum albumin before screening. The medium was not contained blood serum.

As a screening method of this invention is, in particular, a screening method for a compound or the salt which has activity to inhibit or promote proliferation of a vascular smooth cell, comprising;

(A) a process to contact a vascular smooth muscle cell and a thrombin-antithrombin III complex under the absence of blood serum, and under the presence of or under the absence of a test compound, and then measure the degree of proliferation of the cell, and, (B) a process to compare the degree of proliferation of the cell under the presence of a test compound with that under the absence of a test compound.

"To contact" of the above process (A) can be performed by mixing a vascular smooth muscle cell, a test compound and TAT in a solution which does not prevent the natural functions of TAT, and maintaining them under an appreciate reaction condition, for example, at an appropriate reaction temperature for an appropriate reaction time.

The above "a solution which does not prevent the natural functions of TAT" is, for example, MOPS buffer, HEPES buffer, Tris buffer or the like.

The above "an appreciate reaction condition" is not especially restricted, for example, in a solution such as MOPS buffer, HEPES buffer or Tris buffer, at pH 6.0-10.0, preferably at pH 7.0-8.0 and more preferably at pH 7.4 under $CO_2$ concentration 1%-20%, preferably 3%-10% and more preferably 5%, at 4° C.-50° C., preferably at 25° C.-40° C. and more preferably at 37° C., for 1 hour-4 days, preferably for 10 hours-2 days and more preferably for 1 day, or the like. In more detail, a vascular smooth muscle cell is cultured in DMEM medium not containing blood serum and maintained under the above condition.

In a process described the above (A), the order for contacting TAT and a test compound with a vascular smooth muscle cell can be whichever is previous or at a time. However, a test compound preferably contacts with a vascular smooth muscle cell under the presence of TAT. Concentration of TAT contacted with a vascular smooth muscle cell can be usually about 1 ng/ml—about 10 μg/ml and preferably 20 ng/ml— about 2 µg/ml. Time for contacting a vascular smooth muscle cell and TAT is usually for about 1 hour—about 4 days. Concentration of a test compound contacted with a vascular smooth muscle cell can be usually about 0.1 µM—about 100 µM and preferably 1 µM—50 µM. Time for contacting a vascular smooth muscle cell and a test compound is usually for 1 hour—about 4 days and preferably for few hours—about 2 days.

As "a test compound", any substance can be used. For example, an organic compound (amino acid, polypeptide, nucleotide, low molecular weight compound, sugar, high molecular compound or the like), an inorganic compound or the like can be used. For example, a compound library on the market can be used.

In this invention, a method for measuring the degree of proliferation of a vascular smooth muscle cell is not especially restricted and a method which is generally known as a method to measure the degree of proliferation of cells in this field can be used. For example, it is (1) a method to directly measure population of vascular smooth muscle cells, (2) a method to measure population of nuclei of vascular smooth muscle cells, (3) a method to detect metabolic activity of vascular smooth muscle cells or breathing activity of mitochondria in vascular smooth muscle cells with appropriate dye and quantitate, (4) a method to measure the amount of protein or DNA synthesis level in vascular smooth muscle cells or the like. Especially, (2) or (4) is preferable.

(1) A method to directly measure population of vascular smooth muscle cells can be performed, for example, as below. Vascular smooth muscle cells are washed with the washing solution such as a solution containing 140 mM NaCl, 2.7 mM KCl, 10 mM $Na_2HPO_4$ and 1.8 mM $KH_2PO_4$ (pH 7.4) (referred to below as PBS solution). After washing, an appropriate dispersion solution such as a solution containing trypsin and ethylenediamine tetra acetic acid (EDTA) is added to cells and suspended. In this situation, population of vascular smooth muscle cells can be measured, for example, by an automatic cell counting machine such as cell counter (Call Counter, Beckman Coulter, Inc.) or with a cell counting chamber under a microscope.

(2) As a method to measure population of nuclei of vascular smooth muscle cells, at first, cell nuclei are prepared. A method to prepare cell nuclei from vascular smooth muscle cells is, for example, a method with citric acid (Methods Enzymol., vol. 58, p. 143), a method with non-ionic surface active agent (Methods Enzymol., vol. 79, p. 368) or the like. The prepared cell nuclei can be measured with the above cell counter or the like. Additionally, a kit to measure population of the cells by staining nucleic acids with fluorescent dye (CyQUANT™ Cell Proliferation Assay Kit; Wako Pure Chemical Industries, Ltd.) is on the market.

(3) A method to detect metabolic activity of vascular smooth muscle cells or breathing activity of mitochondria in vascular smooth muscle cells with appropriate dye and quantitate is, for example, an alamar blue method (Intern. J. Oncol., vol. 3, p. 473, 1993), MTT method (Experientia, vol. 17, p. 136, 1961), WST-1 method (Chem. Pharm. Bull., vol. 41, p. 1118, 1993) or the like and a kit on the market can be used for any of them.

(4) A method to measure the amount of protein or DNA synthesis level in vascular smooth muscle cells can be performed as below. For example, vascular smooth muscle cells are put on an appropriate size microwell plate. The cells are cultured in an appropriate medium for adhering to a plate, for example, in DMEM medium containing 10% blood serum for 1 day-few days. Next, culture supernatant is removed and the medium is changed to an appropriate basic medium to measure. The basic medium means a medium which can maintain cell survival condition without cell proliferation and it is for example, DMEM medium containing 2% blood serum or the like. After culturing the above vascular smooth muscle cells in the basic medium for 1 hour-2 days, a substance which is an indicator of DNA synthesis level of a cell (e.g., 3H-labeled thymidine) is added to the medium and then the cells are cultured for 1-24 hour(s). After removing culture supernatant, the cells are collected by an appropriate method. For example, the cells are washed with a buffer such as PBS solution and treated with a trypsin solution at 37° C. for 1-5 minute(s) to peel off from well. The cells peeled off are gathered on a grass fiber filter by cell harvester or the like. The radioactivity derived from 3H-labeled thymidine in the cells gathered can be measured by a liquid scintillation counter. Alternatively, vascular smooth muscle cells after washing are treated with TCA (trichloroacetic acid) or the like and precipitated. After that, the cells are dissolved with an alkaline solution such as NaOH solution and the solution is neutralized to obtain cell lysate. The radioactivity come from 3H-labeled thymidine in the cell lysate can be measured by a liquid scintillation counter.

Another embodiment of (4) is a method for measuring specific protein level or specific DNA synthesis level in vascular smooth muscle cells. Specific protein or DNA is Glypican 3 specifically expressed in vascular smooth muscle cells which responds to TAT and proliferates, DNA coding Glypican 3 or the like. A method for measuring specific protein level or specific DNA synthesis level can be any method which is a well-known method as an immunological measuring method to detect protein or as a molecular-biological measuring method to detect mRNA. For example, a molecular-biological measuring method is Polymerase Chain Reaction (PCR), northern blotting, dot blot, analysis method with microarray or macroarray or the like. An immunological measuring method is ELISA method with a microtiter plate, RIA method, fluorescent antibody technique, Western blotting, immunohistologic staining method or the like.

By comparing the degree of proliferation of a vascular smooth muscle cell which was contacted with a test compound measured by the above method (referred to below as Measured value 1) with the degree of proliferation of a vascular smooth muscle cell which was not contacted with a test compound (referred to below as Measured value 2), inhibiting ability of vascular smooth muscle cell proliferation of the test compound can be evaluated. Inhibiting ability of vascular smooth muscle cell proliferation of the test compound can be calculated with the above measured values according to the following Formula 1.

Vascular Smooth Muscle Cell Proliferation Inhibition Ratio(%)={(Measured value 2-Measured value 1)/Measured value 2}×100     [Formula 1]

By the above method, existence or nonexistence of inhibiting ability of vascular smooth muscle cell proliferation of various test compounds, or existence or nonexistence of promoting ability of vascular smooth muscle cell proliferation of them is measured. As a result, a substance having inhibiting or promoting ability of vascular smooth muscle cell proliferation can be screened. For example, a substance whose inhibition ratio of vascular smooth muscle cell proliferation of a test compound is 30% or more and preferably 50% or more can be selected as a substance with inhibiting ability of vascular smooth muscle cell proliferation. A substance selected as above has inhibiting ability of vascular smooth muscle cell proliferation and can be used as an active ingredient of an inhibitor of an arteriosclerotic disease. Additionally, for example, a substance whose inhibition ratio of vascular smooth muscle cell proliferation of a test compound is −30% or less and preferably −50% or less can be selected as a substance with promoting ability of vascular smooth muscle cell proliferation. A substance selected as above has promoting ability of vascular smooth muscle cell proliferation and can be used as an active ingredient of a wound healing agent.

The present invention relates a screening method characterized by that a vascular smooth muscle cell is stimulated by TAT. As the detecting method or the like, well-known methods can be used. The present invention is useful especially for a screening of a large number of compounds and especially for high throughput screening (HTS). A candidate compound can be effectively selected with this invention.

A compound or the salt obtained by a screening method of this invention can be a compound or the salt which inhibits vascular smooth muscle cell proliferation by TAT and shows therapeutic or preventive activity against arteriosclerotic diseases. Therefore, a compound or the salt obtained by the above screening method provides a pharmaceutical composition for therapy or prevention against an arteriosclerotic disease.

An "arteriosclerotic disease" means a generic name of diseases which bring hematogenous disorder in a tissue or an entire organ by that artery loses elasticity because of a risk factor of arteriosclerosis and becomes hard, by that various substances deposits inside artery and path of the blood vessel becomes narrow (stenosis) or blocks (blockade), by that arterial wall partially extends like a "swelling" (aneurism), by that entire artery extends (ectasis) or by that intima is cracked and media splits (dissection) or bursting (bleed). For example, it is atheroma arteriosclerosis, diabetic vascular injury, ischemic stroke, angina, myocardial infarction, cerebral infarction, cerebral hemorrhage or the like.

Additionally, by a screening method of this invention, a compound or salt which promotes proliferation of a vascular smooth muscle cell by TAT and show healing activity of wound can be obtained. Therefore, a compound or the salt obtained by the above screening method provides a pharmaceutical composition for healing of wound.

A pharmaceutical composition containing a compound or a salt thereof obtained by the screening method of this invention as an active ingredient has a beneficial effect that it can be act through inhibition of function of TAT against the above disease related to proliferation of vascular smooth muscle cells. Additionally, the pharmaceutical composition has a beneficial effect that it can act through inhibition of the function against the arteriosclerotic disease, especially proliferation of a vascular smooth cell by TAT. Therefore, a pharmaceutical composition has a beneficial effect that it can improve anti-arteriosclerotic disease on the different mechanism of action from an existent drug for an arteriosclerotic disease on the basis of the other mechanism.

On the other hand, a pharmaceutical composition containing a compound or a salt thereof obtained by the screening method of this invention as an active ingredient has a beneficial effect that it can be act through promotion of function of TAT against the above disease related to proliferation of vascular smooth muscle cells. Additionally, the pharmaceutical composition has a beneficial effect that it can act through promotion of the function against healing of wound, especially proliferation of a vascular smooth cell by TAT. Therefore, the a pharmaceutical composition has a beneficial effect that it can improve healing of wound on the different mechanism of action from an existent drug for healing of wound on the basis of the other mechanism.

The content of the above compound or the salt in the above pharmaceutical composition can be suitably controlled depending on a disease which is a therapeutic purpose, age, body weight of the patient or the like. It may be effective dose for therapy. In case of a low-molecular compound or a high-molecular compound, it is, for example, 0.0001-1000 mg and preferably 0.001-100 mg. In case of a polypeptide or the derivative, it is, for example, 0.0001-1000 mg and preferably 0.001-100 mg.

The above pharmaceutical composition can additionally comprise different auxiliaries which can maintain stably the above compound or a salt thereof. To be more precise, it is a pharmaceutical acceptable auxiliary with the character that it inhibits degradation of the active ingredient before reaching a part which is an object to send the active ingredient. For example, it is an excipient, a binding agent, a stabilizing agent, a buffer agent, a solubilizing agent, an isotonic agent or the like.

Administration of the above pharmaceutical composition is suitably selected depending on a kind of an active ingredient; an individual, an organ, a local part or an organization which is an object of administration; the age or the body weight of an individual who is an object of administration or the like. The above administration is, for example, hypodermic injection, muscle injection, intravenous injection, local administration or the like.

Furthermore, the dosage of the above pharmaceutical composition is also suitably selected depending on a kind of an active ingredient; an individual, an organ, a local part or an organization which is an object of administration; the age or the body weight of an individual who is an object of administration or the like. The dosage is not especially restricted. It is at few times per 1 day, for example, at 1-3 time(s) or the like. The dosage of the active ingredient at one time is, for example, 0.0001-1000 mg/kg weight and preferably 0.001-100 mg/kg weight when the active ingredient is a low-molecular compound or a high-molecular compound. It is, for example, 0.0001-1000 mg/kg weight and preferably 0.001-100 mg/kg weight when the active ingredient is a polypeptide or the derivative.

In the other embodiment except for the above screening method, this invention includes a kit for a screening method of this invention. For example, it is a kit comprising TAT or a kit comprising a vascular smooth muscle cell which responds to TAT and proliferates. The kit can be used for a screening for a compound or the salt which has activity to inhibit or promote proliferation of a vascular smooth muscle cell.

Furthermore, in the other embodiment, this invention provides a growth promoter of a vascular smooth muscle cell containing TAT. That is to say, TAT can be used to promote proliferation of a vascular smooth muscle cell. The promoter can be contained a buffer or the like.

Furthermore, in the other embodiment, this invention includes the use of TAT to promote vascular smooth muscle cell proliferation and a method for promoting of vascular smooth muscle cell proliferation by giving TAT.

Example 1

Preparation of Rat Vascular Smooth Muscle Cells

From JCL-SD rat sacrificed by blood removal under anesthesia with pentobarbital, thoracic aorta is obtained and inner part of blood vessel opened is lightly rubbed by edge of a surgical knife to remove endothelial cells. Furthermore, outer membrane is removed under a stereoscopic microscope to obtain a tissue consisting only media. After media cutting into pieces by scissors is incubated in an enzyme solution (1 mg/ml collagenase, 0.5 mg/ml elastase, 0.4 mg/ml soybean trypsin inhibitor, 2 mg/ml bovine serum albumin) for 3 hours at 37° C., it is centrifuged at 1000 rpm for 5 minutes to obtain vascular smooth muscle cells. The obtained vascular smooth muscle cells were cultured in Dulbecco's Modified Eagle Medium medium (SIGMA CORPORATION) (referred to below as DMEM) containing 10% fetal calf serum (ICN) at 37° C. under 5% $CO_2$.

Example 2

Cloning of Rat Vascular Smooth Muscle Cells

Five hundred cultured rat vascular smooth muscle cells obtained in Example 1 are suspended in 100 ml DMEM and 10% fetal calf serum and plated in ten 96-well plates. By culturing under the same condition as Example 1, the cells proliferated. A Clone which was confirmed by observation with a microscope that the clone clearly proliferated from 1 cell was selected. After the clone proliferated to a degree that cells occupied about half of a well, they were removed from a plate with trypsin EDTA solution (GIBCO), plated into a plate with larger culture area and proliferated to use the following experiments.

Example 3

Purification and Identification of a Specific Proliferation Factor for High Proliferation Clone With cells (high proliferation clones) which react to low concentration (0.1-0.5%) fetal calf serum and proliferate in clones obtained in Example 2, a specific proliferation factor for a high proliferation clone containing fetal calf serum was purified. By diluting fetal calf serum (20 ml) with 40 mM Hepes, pH 7.4 (20 ml) and loading onto a HiTrap Heparin (Amersham Biosciences K.K.), proteins with specific proliferation activity for a high proliferation clone was absorbed to the column. Proteins absorbed were eluted with a concentration gradient of sodium chloride and a protein of this activity was eluted with about 0.6 M sodium chloride. After gathering the active fraction, it was separated by chromatography (20 mM sodium acetate, 0.05-1.0 M sodium chloride) with SP-sepharose (Amersham Biosciences K.K.). As a result, a protein with proliferation promoting activity was eluted with about 0.5 M sodium chloride. After concentrating the active fraction by centricon (Amicon), it was separated by gel filtration chromatography with Superose 12 (Amersham Biosciences K.K.). As a result of analyzing an amino acid sequence of the protein containing the active fraction eluted from Superose 12, the amino acid sequence of thrombin and antithrombin III was detected. Furthermore, molecular weight of the protein was examined by SDS polyacrylamide gel electrophoresis and the molecular weight turned out to be about 80,000. From these results, this protein is thought to be a thrombin-antithrombin III complex (referred to below as TAT).

Example 4

Preparation of Human TAT

By coincubating human thrombin (SIGMA CORPORATION) and human antithrombin III (SIGMA CORPORATION) at 37° C. for 3 hours, these proteins automatically formed a complex. Formation of TAT was confirmed by SDS polyacrylamide gel electrophoresis. Thrombin remained was deactivated by adding 0.2 mM PPACK (CALBIOCHEM) and then thrombin and antithrombin III remained was removed by a column chromatography with HiTrap Heparin and Superose 12 to prepare TAT.

Example 5

Measurement of Proliferation Reaction of Vascular Smooth Muscle Cells by Human TAT Vascular smooth muscle cells were plated in a 96-well plate at a density of $2 \times 10^3$/well and cultured under the same condition as Example 1. After 3 days, the medium was changed with DMEM containing 0.05% bovine serum albumin. After culturing for one more day, the medium was changed again with new DMEM containing 0.05% bovine serum albumin and TAT was added thereto. After 20 hours from addition of TAT, 0.05 µCi/well [methyl 3H] thymidine was added thereto and the cells were cultured for 2 hours. After washing cells twice with 5% trichloroacetic acid, Super mix (PerkinElmer, Inc.) was added thereto and radioactivity derived from [methyl 3H] thymidine taken in cells was measured by Micro Beta (PerkinEimer, Inc.) (FIG. 1).

Example 6

Expression of Glypican 3 in TAT Reactive Cell Clone mRNA samples were prepared from TAT reactive clones and TAT nonreactive clones (3 clones each), analysis of genes expressing in each cells was carried out with rat oligo DNA microarray (Agilent Technologies). As the result, Glypican 3 was found as one of genes expressed in TAT reactive clones more than in TAT nonreactive clones.

Furthermore, mRNA of Glypican 3 in the above samples as measured by real time PCR and it was confirmed that Glypican 3 almost specifically expressed in TAT reactive clones.

Example 7

Preparation of shRNA Expression Adenovirus (RGD Type)

Mouse U6 promoter was inserted at an EcoRI, NotI site of pShuttle vector (Clontech Laboratories, Inc.) and a BamH1, NotI site was introduced at the downstream to construct pShuttle-U6 Vector. shRNA sequence (small hairpin sequence) was inserted at the BamH1, NotI site.

DNA fragment coding shRNA was constructed by annealing oligo DNAs.

Oligo DNAs described SEQ ID: 1 and 2 were annealed to a broken line part (21 bp) in FIG. 2 and they were cloned at a BamHI, NotI site of pShuttle-U6 Vector to construct oligo DNAs.

In this experiment, a sequence described in SEQ ID: 1 was used as GFPi and a sequence described in SEQ ID: 2 was used as GPC3i.

After cloning to pShuttle, by a usual method, a fragment cut by PI-Sce1, I-Ceu1 was inserted at a PI-Sce1, I-Ceu1 site of Adx-(RGD type) adenovirus vector and the vector was cloned. After digesting this adenovirus vector by Pac1, it was transformed into 293 cells and adenovirus was prepared by a usual method.

Reference (A Document as to Adx-(RGD Type) Adenovirus Vector)

Mizuguchi H, Koizumi N, Hosono T et al (2001a) A simplified system for constructing recombinant adenovirus vectors containing heterologous peptides in the H1 loop of their fiber knob. Gene Ther 8: 730-735

Example 8

Purification of Adenovirus and Measurement of Titer

Adenovirus was used after purifying by ultracentrifugation and dialyzing with PBS. Adenovirus rapid titer kit of Clontech Laboratories, Inc. was used with 293 cells for measurement of titer.

Example 9

Determination of M.O.I (Multiplicity of Infection) Against Vascular Smooth Muscle Cells of Adenovirus It was determined by infecting Adx-RGD-LacZ adenovirus to the cell and coloring with LacZ 3 days after infection.

Example 10

Measurement of Knockdown Ratio of GPC3 in Vascular Smooth Muscle Cells

Real-time PCR was carried out 4 day after infection and GPC3 mRNA was determined by RT-PCR. G3PDH was used as an internal standard.

Example 11

Measurement of Cell Proliferation Potency

Adenovirus carrying GFPi or GPC3i was added to cells on a 10 cm laboratory dish at infectious MOI=10 to infect. The cells were moved on a 24-well plate 1 day after infection and cultured under the absence of blood serum for 24 hours. After that, thymidine taken in cells by the stimulus of TAT was measured.

Each of adenovirus inserted shRNA of Glypican 3 (GPC3) (GPC3i), adenovirus inserted shRNA of Green fluorescent protein (GFP) (GFPi) and adenovirus not inserted shRNA (LacZ) was infected to TAT reactive rat vascular smooth muscle cell clones. Cell proliferation potency by TAT was measured by uptake of [methyl 3H] thymidine according an experiment method.

As the result, as FIG. 3 shows, it was confirmed that cell proliferation by stimulus of TAT was remarkably decreased in cells infected GPC3i to inhibit expression of GPC3 compared to cells infected GFPi or LacZ used as a control.

Example 12

Measurement of Inhibitory Activity of a Compound Against Proliferation Promoting Activity of TAT Proliferation inhibitory activity or proliferation promoting activity of a test compound is obtained by carrying out the same measurement as Example 5 and comparing radioactivity when a test compound is added before or after addition of TAT, and radioactivity when a compound is not added.

INDUSTRIAL APPLICABILITY

With a screening method of this invention, a compound which inhibits or promotes proliferation of a vascular smooth muscle cell through a mechanism related to TAT can be screened. A vascular smooth muscle cell growth inhibitor screened can be used as a therapeutic or preventive agent for an arteriosclerotic disease. Additionally, a vascular smooth muscle cell growth promoter screened can be used as a wound healing agent.

The invention claimed is:

1. A screening method for a compound or a salt thereof that has activity to inhibit or promote proliferation of a vascular smooth muscle cell, comprising;
   contacting a vascular smooth muscle cell with a thrombin-antithrombin III complex, wherein said complex is substantially free of free thrombin and of heparin, in the absence of blood serum and in the presence or absence of a test compound, and then measuring the degree of proliferation of the cell, and;
   comparing the amount of proliferation of the cell in the presence of the test compound with the level of proliferation in the cell in the absence of the test compound;
   wherein an increase in the amount of proliferation of the cell in the presence of the test compound than in the absence of the test compound indicates that the test compound is a promoter of vascular smooth muscle cell proliferation and wherein a decrease in the amount of proliferation of the cell in the presence of the test compound than in the absence of the test compound indicates that the test compound is an inhibitor of vascular smooth muscle cell proliferation.

2. The screening method of claim 1, wherein the cell is a cell which proliferates in response to addition of 0.1 to 0.5% blood serum to a medium in which the cell is cultured.

3. The screening method of claim 1, wherein the thrombin-antithrombin III complex is a human thrombin-antithrombin III complex.

4. The screening method of claim 1, wherein the cell is one that expresses Glypican-3.

5. The screening method of claim 4 wherein the cell comprises a vector expressing a Glypican-3 protein.

6. The screening method of any one of claims 1-5, wherein the degree of proliferation of a vascular smooth muscle cell is measured by measuring the DNA synthesis level of the vascular smooth muscle cell.

7. The screening method of any one of claims 1-5, wherein the degree of proliferation of the vascular smooth muscle cell is measured by measuring the cell population of the vascular smooth muscle cells.

* * * * *

```
                        SEQUENCE LISTING

<160> NUMBER OF SEQ ID NOS: 2

<210> SEQ ID NO 1
<211> LENGTH: 21
<212> TYPE: DNA
<213> ORGANISM: artificial sequence
<220> FEATURE:
<223> OTHER INFORMATION: oligoDNAfor GFPi

<400> SEQUENCE: 1
ggcgatgcca cctacggcaa g                                            21

<210> SEQ ID NO 2
<211> LENGTH: 21
<212> TYPE: DNA
<213> ORGANISM: artificial sequence
<220> FEATURE:
<223> OTHER INFORMATION: oligoDNA for GPC3i

<400> SEQUENCE: 2
gaactacacc aatgccatgt t                                            21
```